United States Patent

Holzner et al.

[11] Patent Number: 6,090,345
[45] Date of Patent: Jul. 18, 2000

[54] PHOSPHORUS-CONTAINING COMPOUNDS BASED ON 1-HYDROXYPROPANE-1, 3-DIPHOSPHONIC ACID

[75] Inventors: Christoph Holzner, Köln; Armin Spaniol, Bergisch-Gladbach; Hans Dahmen, Köln, all of Germany

[73] Assignee: Bayer AG, Germany

[21] Appl. No.: 09/240,285

[22] Filed: Jan. 29, 1999

[30] Foreign Application Priority Data

Feb. 3, 1998 [DE] Germany .......................... 198 04 124

[51] Int. Cl.⁷ .................. C23F 11/167; C09K 21/12; C07F 9/28; C07F 9/38
[52] U.S. Cl. .................. 422/15; 106/14.12; 252/389.22; 252/289.23; 252/609; 562/20; 562/8; 562/23
[58] Field of Search .................. 562/20, 8, 23; 252/389.22, 389.23, 609; 106/14.12; 422/15

[56] References Cited

U.S. PATENT DOCUMENTS

| | | | |
|---|---|---|---|
| 3,346,487 | 10/1967 | Irani et al. | 252/8.5 |
| 3,532,639 | 10/1970 | Hatch | 252/389 |
| 4,022,606 | 5/1977 | Conrad et al. | 424/320 |
| 4,141,967 | 2/1979 | Osberghaus et al. | 424/47 |
| 4,229,409 | 10/1980 | Scharf et al. | 422/13 |
| 4,536,348 | 8/1985 | Blum | 252/32.5 |
| 4,559,181 | 12/1985 | Leroux . | |
| 4,642,229 | 2/1987 | Cumming et al. | 424/1.1 |
| 4,689,200 | 8/1987 | Cook et al. | 422/15 |
| 4,828,795 | 5/1989 | Cook et al. | 422/15 |
| 5,154,843 | 10/1992 | Rizvi et al. | 252/32.5 |
| 5,386,038 | 1/1995 | Davis et al. | 549/262 |
| 5,606,105 | 2/1997 | Davis et al. | 562/8 |
| 5,935,656 | 8/1999 | Koerner et al. | 427/384 |

FOREIGN PATENT DOCUMENTS

| | | |
|---|---|---|
| 074 336 | 3/1983 | European Pat. Off. . |
| 491 391 | 6/1992 | European Pat. Off. . |
| 30 44 214 | 6/1982 | Germany . |
| 141 200 | 5/1985 | Germany . |

OTHER PUBLICATIONS

German Search Report for foreign counterpart application No. 99 10 1117.2 (May 10, 1999).
Chemical Abstracts, vol. 083, No. 10, Columbus, OH, XP–002101283, abstract No. 081146, *Fireproofing of Textiles*, Kenzo Sato, Yugaro Masuda and Sato Takashi (Sep. 8, 1975).
Derwent WPAT English Abstract for EP 141 200 (May 15, 1985).
Derwent WPAT English Abstract for DE 30 44 214 (See Ref. I) (1982).
Derwent WPAT English Abstract for EP 491 391 (See Refs. A, C, and H) (1993).
Derwent WPAT English Abstract for EP 074 336 (See Refs. B, D, and G) (1983).

*Primary Examiner*—Joseph D. Anthony
*Attorney, Agent, or Firm*—Connolly Bove Lodge & Hutz LLP

[57] ABSTRACT

The present invention relates to phosphorus-containing compounds based on 1-hydroxypropane-1,3-diphosphonic acid and to the acid itself of general formula (I)

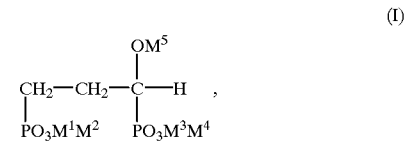

in which
$M^1$, $M^2$, $M^3$, $M^4$ and $M^5$, independently of one another, each denote a radical from the series hydrogen, alkali metal, an equivalent of ammonium, alkyl- or hydroxyalkyl-substituted ammonium,
a process for the preparation thereof, novel intermediates and the use thereof as a corrosion inhibitor, scale inhibitor and as a flame retardant.

19 Claims, No Drawings

PHOSPHORUS-CONTAINING COMPOUNDS BASED ON 1-HYDROXYPROPANE-1, 3-DIPHOSPHONIC ACID

The present invention relates to phosphorus-containing compounds based on 1-hydroxypropane-1,3-diphosphonic acid and to the acid itself, a process for the preparation thereof, novel intermediates and their use as a corrosion inhibitor, scale inhibitor and as a flame retardant. 1-Hydroxyphosphonic acids with the structural element

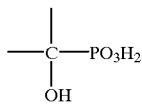

are widely used in water treatment. 1-Hydroxyethane-1,1-diphosphonic acid (HEDP), for example, is used to inhibit boiler scale formation in cooling water (P. R. Puckorius, S. D. Strauss; Power, May 1995, page 17 ff.). Hydroxyphosphonoacetic acid is known as a corrosion inhibitor for metals (cf. EP 0 074 336). It is a disadvantage of the two compounds that they each display good activity in only one discipline: HEDP is a good scale inhibitor but a poor corrosion inhibitor, whereas hydroxyphosphonoacetic acid displays good corrosion protection but only slight protection against lime scale.

The object of the present invention was to find novel, phosphorus-containing compounds based on a 1-hydroxyphosphonic acid which exhibit both good corrosion inhibition and scale inhibition, and also to provide as simple a process as possible for the preparation thereof.

Surprisingly, this object was achieved by phosphorus-containing compounds based on 1-hydroxypropane-1,3-diphosphonic acid.

The present invention provides compounds of formula (I)

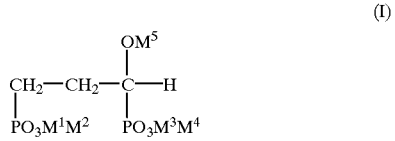

in which
$M^1, M^2, M^3, M^4$ and $M^5$, independently of one another, each denote a radical from the series hydrogen, alkali metal, an equivalent of an alkaline earth metal, ammonium, alkyl- or hydroxyalkyl-substituted ammonium salts.

In the salts, the five acid protons of the 1-hydroxypropane-1,3-diphosphonic acid may be completely or partly replaced by cations. Preferred compounds of formula (I) are compounds in which $M^1, M^2, M^3, M^4$ and $M^5$ each denote hydrogen or lithium, sodium, potassium, magnesium, calcium, ammonium, methylammonium, ethylammonium, trimethylammonium, triethylammonium, n-butylammonium, n-hexylammonium, octylammonium, ethanolammonium, diethanolammonium, triethanolammonium or morpholinium.

Compounds of formula (I) in which $M^1, M^2, M^3, M^4$ and $M^5$ denote hydrogen, sodium or triethanolammonium are especially preferred.

The phosphorus-containing compounds of general formula (I) may be simply prepared from cheap, readily available raw materials. Acrolein is first reacted with at least one equivalent of a dialkyl phosphite in the presence of a basic catalyst. The reaction mixture obtained is then reacted with at least one further equivalent of dialkyl phosphite in the presence of a radical former or under UV irradiation. Finally, after distilling off any excess dialkyl phosphite present, the reaction mixture is hydrolysed with water, aqueous mineral acid or aqueous alkaline lye.

Dimethyl, diethyl, dipropyl and dibutyl phosphite are preferably used as the dialkyl phosphite in the first two reaction steps, particularly preferably dimethyl phosphite. The first two reaction steps are preferably carried out under a protective gas such as argon or nitrogen and without the use of an inert solvent. The first two reaction steps may naturally also be carried out in an ether such as, for example, diethyl ether or in an aromatic hydrocarbon such as, for example, toluene as solvent. Before the third reaction step, the hydrolysis, however, these solvents must be removed by distillation.

In the first reaction step, the quantity of dialkyl phosphite used is preferably 1 to 1.5 mol. per mol. of acrolein used. The sodium alcoholates corresponding to the dialkyl phosphites are preferably used as the basic catalysts, particularly preferably sodium methylate. The use of amines or of solid potassium fluoride as the basic catalysts is also possible. The alcoholates are preferably used in quantities of 5 to 100 mmol. per mol. of acrolein, particularly preferably 10 to 30 mmol./mol. The amines and potassium fluoride are preferably used in quantities of 100 to 1000 mmol. per mol. of acrolein, particularly preferably in quantities of 200 to 500 mmol. per mol. of acrolein. Unlike the other catalysts, potassium fluoride has to be removed by filtration after the first step of the synthesis. The amines may remain in the product. The temperature during the first reaction step is preferably 0 to 80° C., particularly preferably 20 to 40° C.

In the second reaction step, 1 to 4 mol. dialkyl phosphite per mol. acrolein originally used is added to the reaction mixture from reaction step one. The radicals needed to start the reaction may be produced by UV irradiation of the reaction mixture. Preferably, however, a radical former is added as catalyst. Suitable catalysts are organic peroxides such as di-tert.-butyl peroxide, tert.-butyl hydroperoxide, benzoyl peroxide or tert.-butyl per(2-ethyl)hexanoate or other radical formers such as α,α'-azodiisobutyronitrile. The catalysts are preferably used in quantities of 0.1 to 10 mole %, based on original acrolein, at temperatures of 50 to 180° C. The simultaneous addition of a basic substance such as, for example, sodium methylate is also advantageous. Any excess of dialkyl phosphite present may be distilled off under reduced pressure and recovered after adding the catalyst. After this second reaction step, a complex phosphonic acid ester mixture is obtained which no longer contains any compounds with C=C double bonds.

In the third reaction step the complex phosphonic acid ester mixture is heated with water, aqueous mineral acid or aqueous alkaline lye at temperatures of preferably 90 to 150° C. and the resulting alcohol-water mixture is simultaneously distilled off. The hydrolysis may also be performed under increased pressure. An aqueous solution of 1-hydroxypropane-1,3-diphosphonic acid or a solution of the alkali salts thereof is obtained.

The alkali, alkaline earth, ammonium or alkyl-substituted ammonium salts may be prepared by the complete or partial neutralisation of the free acid with the appropriate metal hydroxides or carbonates or with the free amines.

During reaction steps 1 and 2, a phosphonic acid ester mixture of increasing complexity is obtained, which contains the immediately recognisable precursors (II) and (III) of 1-hydroxypropane-1,3-diphosphonic acid or its derivatives in decreasing concentration.

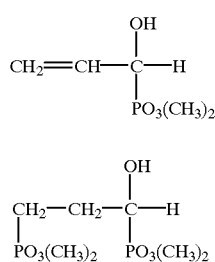

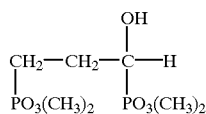

Thus, in Example 1, after the first reaction step the reaction mixture still contains 67% of the phosphorus in compound (II), and after the second reaction step only 28.8% of the phosphorus in compound (III). Surprisingly, during the hydrolysis of the complex mixture from step two, a phosphonic acid mixture is obtained which contains 71.1% of the phosphorus in the form of 1-hydroxypropane-1,3-diphosphonic acid (I). A relatively homogeneous substance is therefore formed from a complex mixture by hydrolysis alone, without an additional purification step. Impurities which may occur in this crude product, mainly phosphonic acid but also various unidentified phosphonic acids and phosphorous acid, may remain in the agent while being used according to the invention.

An advantageous feature of the preparation process according to the invention is that there are already virtually no more C=C double bonds detectable in the reaction mixture after the second reaction step. Both the ester mixture from step two and the 1-hydroxypropane-1,3-diphosphonic acid from step three are free from unsaturated compounds.

1-Hydroxypropane-1,3-diphosphonic acid and its salts may be used to prevent metal corrosion and scale formation in aqueous systems. For this purpose the 1-hydroxypropane-1,3-diphosphonic acid or its salts are added to the aqueous system in a concentration of 0.1 to 50000 ppm. The concentration of 1-hydroxypropane-1,3-diphosphonic acid in the aqueous system is preferably 1 to 500 ppm, particularly preferably 1 to 100 ppm. Such agents may also contain phosphoric acid or a water soluble salt thereof, preferably in a concentration of from 0,1 up to 20 000 ppm.

Aqueous systems that can be treated against corrosion and scale formation simultaneously according to the invention are cooling water systems, steam-producing systems, sea-water evaporators, gas-washing systems and heating systems.

1-Hydroxypropane-1,3-diphosphonic acid and its salts may be used alone or together with other compounds suitable for the treatment of aqueous systems. In addition to 1-hydroxypropane-1,3-diphosphonic acid, for example, the aqueous system may also contain dispersants such as water-soluble polyacrylates, polymethacrylates, polyaspartates or copolymers of acrylamide with acrylic acid; sequestrants such as nitrilotriacetic acid or ethylenediaminetetraacetic acid; antifoams such as polydimethyl siloxanes or distearylsebacamide; biocides such as amines, triazines, chlorophenols or chlorine-releasing substances; oxygen-binding substances such as hydrazine or alkali metal sulfites. Other corrosion inhibitors such as water-soluble zinc salts; phosphates, polyphosphates; phosphonic acids and their salts such as nitrilotrismethylene-phosphonic acid; phosphonocarboxylic acids such as phosphonosuccinic acid, phosphonopropionic acid or hydroxyphosphonoacetic acid; chromates such as sodium chromate; nitrites such as sodium nitrite; benzotriazoles, bis-benzotriazoles or copper-deactivating benzotriazole or tolutriazole derivatives; N-acyl sarcosines; N-acyl-iminodiacetic acids; ethanolamines or fatty acid amines; oligomers of maleic acid with phosphorous acid containing phosphonate groups, as in EP 491 391 or cooligomers of acrylic acid with maleic acid containing phosphonate groups according to DE-OS 3 044 214 may also be contained in the aqueous system. Other scale inhibitors such as 2-phosphonobutane-1,2,4-tricarboxylic acid, 1-hydroxyethane-1,1-diphosphonic acid or diethylenetriaminepenta(methylenephosphonic acid) may also be added to the aqueous system.

In addition, 1-hydroxypropane-1,3-diphosphonic acid and its salts may be used as a flame retardant for plastics such as polyurethanes or epoxy resins. The calcium, magnesium, aluminum or trialkylammonium salts of 1-hydroxypropane-1,3-diphosphonic acid are preferably used. For this purpose they are added to the plastics intermediates in dehydrated form.

The phosphonic acid ester mixture obtained after the second reaction step, which represents an intermediate of 1-hydroxypropane-1,3-diphosphonic acid synthesis or of its derivatives and contains 10 to 40% of the phosphorus in the form of a 1-hydroxypropane-1,3-diphosphonic acid pentaalkyl ester, may also be used as a flame retardant for plastics. This phosphonic acid ester mixture from the second reaction step of acrolein with a dialkyl phosphite may be incorporated into the plastics intermediates, such as, for example, polyols during polyurethane production, without pretreatment.

The invention will be explained using the following examples.

EXAMPLE 1

330 g (3 mol.) of dimethyl phosphite are placed in a multinecked flask under nitrogen. Over a period of one hour, 168 g (2.85 mol.) acrolein (approx. 95%, stabilised with 0.2% hydroquinone) and 13.2 g (0.06 mol.) methanolic sodium methylate solution (25%) from two separate dropping funnels are added simultaneously, dropwise, while stirring. The reaction mixture heats up rapidly and is kept at 40° C. by cooling. 30 minutes after completing the addition, a further 1.5 g of sodium methylate solution are added. The reaction mixture is stirred at 30 to 40° C. for a further 2.5 hours. According to $^{31}$P-NMR analysis, 67.1% of the phosphorus is present in the monophosphonate (II), 9.8% in the diphosphonate (III) and 1.5% in dimethyl and monomethyl phosphite. The chemical shift δ (measured in $CDCl_3$ and against 85% $H_3PO_4$ as external standard) for compound (II) is 24.3 ppm (1-P) and for compound (III) 26.7 ppm (1-P) and 35.1 ppm (3-P).

990 g (9 mol.) of dimethyl phosphite and 3.5 g (0.065 mol.) of solid sodium methylate are placed in a second reaction flask. The apparatus is evacuated twice and flushed with nitrogen each time. The dimethyl phosphite is then heated to 10° C. and the phosphonate mixture from the previous step of the synthesis and a solution of 40 g (0.13 mol.) tert.-butyl per(2-ethyl)hexanoate (70%) in 165 g (1.5 mol.) dimethyl phosphite are added simultaneously from two separate dropping funnels. During the 80-minute addition and a 30-minute secondary reaction period, the reaction temperature is kept at 110 to 120° C. Excess dimethyl phosphite is then distilled off, most of it (852.2 g) distilling off at a bottom temperature of up to 75° C. and under a pressure of 20 mbar, the rest up to a bottom temperature of 130° C. tinder a pressure of I mbar. The total mass of the distillate is 895 g and is only slightly higher than the theoretically expected distillate mass of 865 g (825 g (7.5 mol.) dimethyl phosphite+40 g catalyst). According to $^{31}$P-NMR analysis, 28.8% of the phosphorus in the bottom is present in the diphosphonate (III). The chemical shifts δ (measured in CDCl$_3$ and against 85% H$_3$PO$_4$ as external standard) for the two phosphorus atoms in compound (III) are 26.3 ppm (1-P) and 34.5 ppm (3-P). Both phosphorus signals show a P,P long-range coupling with a coupling constant $^J_{PP}$=7.7 Hz. Monophosphonate (II) is not detectable. The $^1$H-NMR spectrum shows no signal for olefinic protons, which means that the C=C double bonds of the acrolein are fully saturated.

For the hydrolysis, 730 g of the bottom product are mixed with 300 g water and heated to 120° C. in distillation apparatus. Over a period of 12 h at 115–120° C., 330 g water per hour are fed continuously into the bottom. At the same time, a methanol-water mixture distils off.

A $^{31}$P-NMR analysis of the hydrolysed bottoms shows that 71.7% of the phosphorus is present in 1-hydroxypropane-1,3-diphosphonic acid (I).

The chemical shifts δ (measured in H$_2$O and against 85% H$_3$PO$_4$ as external standard) for the two phosphorus atoms in compound (I) are 22.6 ppm (1-P) and 30.6 ppm (3-P). Both phosphorus signals show a P,P long-range coupling with a coupling constant $^4J_{PP}$=7.3 Hz. A $^{13}$C-NMR spectrum (measured in H$_2$O with trimethylsilyltetradeuteropropionic acid sodium salt (TSP) as internal standard, adjusted to δ=1.7 ppm) shows the following chemical shifts δ (based on tetramethyl silane (TMS)) and coupling constants J:1-C:δ= 71.76 ppm ($^1J_{CP}$=160.9 Hz, $^3J_{CP}$=17.0 Hz); 2-C: δ=28.88 ppm (t, J$_1$ approximately equal to J$_2$=3.8 Hz); 3-C: 27.23 ppm ($^1J_{CP}$=135.6 Hz, $^3J_{CP}$=13.9 Hz).

In addition to the 1-hydroxypropane-1,3-diphosphonic acid, the solution also contains other phosphonates of unknown structure, which bind an additional 16.9% of the phosphorus, and also H$_3$PO$_3$ (11.2% of the phosphorus) and H$_3$PO$_4$ (0.9%). A total of 88.6% of the phosphorus is bound in phosphonates. From this total phosphonate content, the phosphorus content of the solution (15.5 mass %) and the molar mass of 220.06 g/mol. a phosphonic acid content of 48.8 mass % is calculated. This concentration is used to calculate the amount weighed out in the following application test.

EXAMPLE 2

To test the corrosion-inhibiting action, a synthetic tap water is prepared containing 0.005 mol./l CaCl$_2$, 0.001 mol./l MgSO$_4$, 0.0031 mol./l NaSO$_4$ and 0.0064 mol./l NaHCO$_3$, corresponding to a calculated total hardness of 33.6° German hardness. A small quantity of the inhibitor, pre-neutralised with sodium hydroxide solution, is added to this water so that its initial concentration in the test solution, calculated as free inhibitor acid, is 7.5 ppm. 1-Hydroxypropane-1,3-diphosphonic acid from Example 1, 1-hydroxyethane-1,1-diphosphonic acid (HEDP) and hydroxyphosphonoacetic acid (HEP) are used as inhibitors. The solution is placed in a 12-liter capacity vessel in which 4 steel tube rings of St 37 are moved on a stirrer at a rate of 0.6 n/s. Throughout the duration of the test, 0.4 l/h of fresh solution, containing 5 ppm of the appropriate inhibitor as well as the salts mentioned above, is metered into the vessel and the same quantity is allowed to flow out via an overflow. After 24 h the pH in the vessel liquid is measured. After 72 h the rings are removed, pickled and visually assessed. The weight loss of the rings is determined.

With 1-hydroxypropane-1,3-diphosphonic acid from Example 1 and with HPE, only minimal pitting is visible on the steel rings. The corrosion rates are 0.137 mm/a (at pH 8.43) for 1-hydroxypropane-1,3-diphosphonic acid and 0.136 mm/a (at pH 8.45) for HPE. In the test with HEDP, on the other hand, the steel rings exhibit clear pitting. The rate of corrosion in this case is 0.323 im/a at pH 8.50.

EXAMPLE 3

To test the scale-inhibiting action, a synthetic tap water is prepared containing 0.005 mol./l CaCl$_2$, 0.001 mol./l MgSO$_4$, 0.0031 mol./l Na$_2$SO$_4$ and 0.0064 mol./l NaHCO$_3$. The total hardness of this water is determined to 32.8° German hardness by titration with EDTA. A small quantity of the inhibitor, pre-neutralised with sodium hydroxide solution, is added to this water so that its concentration in the test solution, calculated as free inhibitor acid, is 5 ppm. The solution is adjusted to a pH of 9.0 by adding molar sodium hydroxide solution and is stored for 24 h at 80° C. in a closed glass bottle with a freshly degreased glass rod inserted, in a drying cupboard. After storage, the solution is assessed for crystal deposits and is filtered through a 0.45 μm membrane filter. The pH of the filtrate is measured and the residual total hardness determined by titration. The percentage residual hardness is calculated from the experimental data as follows:

$$RH[\%] = \frac{a-b}{c-b} \times 100$$

a=residual total hardness of the filtered sample with inhibitor b=residual total hardness of a filtered blank test sample without inhibitor c=initial total hardness The higher the RH[%] value of the filtrate, the more effective is the inhibition of scale formation by the inhibitor With 1-hydroxypropane-1,3-diphosphonic acid from Example 1 the solution is clear after storage for 24 hours. The determination of hardness gives 100% of the initial value. The pH has fallen from 9.04 at the beginning of storage to 8.89 after storage.

In the HPE test, crystal formation is observed on the glass walls of the bottle. The percentage residual hardness RH[%] is 63.7%. The pH has fallen markedly from 9.09 to 8.59.

The HEDP solution deposits crystals on the glass wall and a slimy precipitate on the bottom of the bottle after 24 h. The percentage residual hardness RH[%] is 94.1%. The pH has fallen from 9.07 to 8.95.

As can be seen from this example, 1-hydroxypropane-1, 3-diphosphonic acid is the only one of the phosphonic acids tested to provide complete inhibition of CaCO$_3$ deposits. HEDP performs slightly worse in the scale inhibition test, while HPE performs markedly worse.

A comparison of Example 2 with Example 3 shows that 1-hydroxypropane-1,3-diphosphonic acid is the only one of the three phosphonic acids tested to combine good corrosion inhibition with good scale inhibition.

What is claimed is:

1. A phosphorus-containing compound having the formula (I):

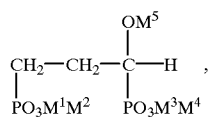

(I)

wherein

M¹, M², M³, M⁴ and M⁵, independently of one another, represent hydrogen, an alkali metal, an alkaline earth metal, ammonium or alkyl- or hydroxyalkyl-substituted ammonium.

2. The phosphorus-containing compound according to claim 1, wherein M¹, M², M³, M⁴ and M⁵ each represent hydrogen, lithium, sodium, potassium, magnesium, calcium, ammonium, methylammonium, ethylammonium, trimethylammonium, triethylammonium, n-butylammonium, n-hexylammonium, octylammonium, ethanolammonium, diethanolammonium, triethanolammonium or morpholinium.

3. The phosphorus-containing compound according to claim 2, wherein M¹, M², M³, M⁴ and M⁵ each represent hydrogen, sodium or triethanolammonium.

4. A process for inhibiting metal corrosion and/or scale formation in an aqueous system, the process comprising adding a corrosion and/or scale formation inhibiting effective amount of the phosphorus-containing compound according to claim 1 to the aqueous system.

5. The process according to claim 4, wherein the effective amount of the phosphorous-containing compound is from 0.1 to 50,000 ppm.

6. The process according to claim 4, wherein the aqueous system is a cooling water system, a stream-producing system, a sea-water evaporator system, a gas-washing system, a cooling system, or a heating system.

7. The process according to claim 4, further including adding a corrosion and/or scale formation inhibiting effective amount of phosphorous acid or a water-soluble salt of phosphorous acid to the aqueous system.

8. The process according to claim 7, wherein the effective amount of the phosphorous acid or the water-soluble salt of phosphorous acid is from 0.1 to 20,000 ppm.

9. A process for preparing a phosphorus-containing compound having the formula (I)

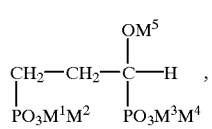

(I)

wherein

M¹, M², M³, M⁴ and M⁵, independently of one another, represent hydrogen, an alkali metal, or an equivalent of an alkaline earth metal, ammonium or alkyl- or hydroxyalkyl-substituted ammonium, the process comprising the steps of:

a) reacting acrolein with at least one equivalent of a dialkyl phosphite in the presence of a basic catalyst to form a first reaction mixture;

b) reacting the first reaction mixture with at least one further equivalent of dialkyl phosphite in the presence of a radical former or under UV irradiation to form a second reaction mixture; and c) hydrolyzing the second reaction mixture with water, an aqueous mineral acid or an aqueous alkaline lye to form the phosphorus-containing compound having the formula (I).

10. The process according to claim 9, wherein the second reaction mixture is hydrolyzed with water or the aqueous mineral acid, and the process further comprises the step of:

d) partially or completely neutralizing the phosphorus-containing compound having the formula (I) with an alkali or alkaline earth hydroxide, ammonia, or an amine.

11. The process according to claim 9, wherein the dialkyl phosphite is dimethyl, diethyl, dipropyl, or dibutyl phosphite.

12. The process according to claim 9, wherein 1 to 1.5 mol. of dialkyl phosphite 30 per mol. of acrolein is used in step a) and 1 to 4 mol. of dialkyl phosphite per mol. of acrolein is used in step b).

13. The process according to claim 9, further comprising between steps b) and c) the step of distilling off excess dialkyl phosphite.

14. The process according to claim 9, wherein the radical former of step b) is an organic peroxide or α,α'-azodiisobutyronitrile.

15. The process according to claim 9, wherein a basic substance is used in addition to the radical former in step b).

16. The process according to claim 9, wherein the basic catalyst of step a) is an alcoholate corresponding to the dialkyl phosphite, an amine or solid potassium fluoride.

17. The process according to claim 16, wherein the basic catalyst is sodium methylate.

18. The process according to claim 16, wherein the alcoholate corresponding to the dialkyl phosphite is present in the amount of 5 to 100 mmol. per mol. of acrolein.

19. A process for providing a flame retardancy in a plastic, the process comprising incorporating into the plastic the phosphorus-containing compound formed in step c), of the process according to claim 9.

* * * * *